(12) United States Patent
Morris

(10) Patent No.: US 11,261,228 B2
(45) Date of Patent: Mar. 1, 2022

(54) INSULIN DERIVATIVES WITH A TERMINAL LPXT MOTIF

(71) Applicant: Arri Russell Morris, Austin, TX (US)

(72) Inventor: Arri Russell Morris, Austin, TX (US)

(*) Notice: Subject to any disclaimer, the term of this patent is extended or adjusted under 35 U.S.C. 154(b) by 53 days.

(21) Appl. No.: 16/719,788

(22) Filed: Dec. 18, 2019

(65) Prior Publication Data

US 2021/0188938 A1 Jun. 24, 2021

(51) Int. Cl.
*C07K 14/62* (2006.01)
*A61K 38/28* (2006.01)
*A61P 3/10* (2006.01)
*C12P 21/02* (2006.01)

(52) U.S. Cl.
CPC .............. *C07K 14/62* (2013.01); *C12P 21/02* (2013.01)

(58) Field of Classification Search
CPC ............ C07K 14/62; A61K 38/28; A61P 3/10
See application file for complete search history.

(56) References Cited

U.S. PATENT DOCUMENTS 7,193,035 B2 * 3/2007 Berchtold .............. C07K 14/62
530/303

* cited by examiner

*Primary Examiner* — Maryam Monshipouri
(74) *Attorney, Agent, or Firm* — Hulsey P.C.

(57) ABSTRACT

The present invention relates to insulin derivatives which, in comparison to insulin glulisine and similar derivatives, has a simplified process for synthesis. In particular, the present invention relates to insulin derivatives or physiologically tolerable salts thereof in which the motif Leucine-Proline-X-Threonine appears at the end of the B-chain, where X is any amino acid residue. Due to the nature of the process, the A-chain and B-chain must begin with a Glycine amino acid residue.

1 Claim, 4 Drawing Sheets

Specification includes a Sequence Listing.

Modified pPIC9K vector

Modified pGAPZα vector

Cleavage sites and folding

```
                              SEQUENCE LISTING

<160> NUMBER OF SEQ ID NOS: 4

<210> SEQ ID NO 1
<211> LENGTH: 182
<212> TYPE: DNA
<213> ORGANISM: Artificial Sequence
<220> FEATURE:
<221> NAME/KEY: CDS
<222> LOCATION: (7)...(171)
<223> OTHER INFORMATION: Codes for single chain peptide with restriction
      enzyme sites EcoRI and NotI included. Ochre stop codon closes
      readingframe.
<313> RELEVANT RESIDUES IN SEQ ID NO: 7 TO 171

<400> SEQUENCE: 1 gaattc ttg cca gag act ggt gtc aag cag cac ttg tgt ggt tct cat ttg     51
       Leu Pro Glu Thr Gly Val Lys Gln His Leu Cys Gly Ser His Leu
         1               5                  10                  15 gtt gag gcc ttg tac ttg gtt tgt ggt gag aga ggt ttc ttc tac ctg cca  102
Val Glu Ala Leu Tyr Leu Val Cys Gly Glu Arg Gly Phe Phe Tyr Leu Pro
                20                  25                  30 gaa acc ggt atc gtt gag cag tgt tgt act tcc atc tgt tcc ctg tac cag  153
Glu Thr Gly Ile Val Glu Gln Cys Cys Thr Ser Ile Cys Ser Leu Tyr Gln
        35                  40                  45 ttg gag aac tac tgt aac taagcggccgc                                   182
Leu Glu Asn Tyr Cys Asn
 50                  55
```

```
<210> SEQ ID NO 2
<211> LENGTH: 55
<212> TYPE: PRT
<213> ORGANISM: Artificial Sequence
<220> FEATURE:
<223> OTHER INFORMATION: The expressed single chain peptide, does not
      include result of fusion to MAT-alpha secretion factor via EcoRI

<400> SEQUENCE: 2

Leu Pro Glu Thr Gly Val Lys Gln His Leu Cys Gly Ser His Leu Val
1               5                   10                  15

Glu Ala Leu Tyr Leu Val Cys Gly Glu Arg Gly Phe Phe Tyr Leu Pro
            20                  25                  30

Glu Thr Gly Ile Val Glu Gln Cys Cys Thr Ser Ile Cys Ser Leu Tyr
        35                  40                  45

Gln Leu Glu Asn Tyr Cys Asn
    50                  55

<210> SEQ ID NO 3
<211> LENGTH: 21
<212> TYPE: PRT
<213> ORGANISM: Human

<400> SEQUENCE: 3

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 4
<211> LENGTH: 30
<212> TYPE: PRT
<213> ORGANISM: Human

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

INSULIN DERIVATIVES WITH A TERMINAL LPXT MOTIF

STATEMENT REGARDING FEDERALLY SPONSORED RESEARCH OR DEVELOPMENT

Not applicable

REFERENCE TO SEQUENCE LISTING, A TABLE, OR A COMPUTER PROGRAM LISTING COMPACT DISC APPENDIX

The file "seqlist.txt", last modified Dec. 16, 2019 contains the sequence listings referenced in this application and is 1,312 bytes.

SEQ ID No. 1 is a synthetic gene designed to express a single chain peptide.

SEQ ID No. 2 is the expressed single chain peptide.

SEQ ID No. 3 is the A chain of human insulin.

SEQ ID No. 4 is the B chain of human insulin.

RELATED APPLICATIONS

| U.S. Pat. No. 6,221,633B1 | April 2001 | Ertl et al. |
| US 2015/0118710 A1 | April 2015 | Govindappa et al. |

BACKGROUND

The incidence of diabetes mellitus has risen from approximately 108 million patients in 1980 to an estimated 422 million in 2014. Meanwhile, cost-related insulin underuse is reported to affect one in four American patients with diabetes. The concurrent advent of insulin rationing-related deaths calls for new, cost-effective approaches to the synthesis of insulin derivatives.

The present invention relates to insulin derivatives which, in comparison to current derivatives, have a simplified process for synthesis that relies heavily on recombinant DNA technology. Although there are many novel insulin derivatives that could be created in a number of hosts by following the process, the present disclosure will focus on a derivative similar to insulin glulisine expressed in a yeast host organism, *Pichia pastoris*. A key aspect of the structure is the Leucine-Proline-X-Threonine motif, where X is any amino acid residue.

The commercial manufacturing process for insulin glulisine requires 15 steps that broadly fall under the categories: cell culture and harvest, downstream processing, and final purification. In summary, the insulin glulisine fusion protein is expressed by *Escherichia coli* and stored in inclusion bodies within the *E. coli* cells. The fusion protein is folded and then enzymatically converted during downstream processing. The product of the downstream processing is then purified by chromatography, usually at a separate facility.

The novel use of sortase from *Staphylococcus aureus* eliminates the need for downstream processing, can be performed at a single facility, and reduces expenditure for catalysts.

U.S. Pat. No. 6,221,633B1 describes insulin glulisine and alternative fast-acting insulin compounds. The insulin derivatives described by claim 1 differ from the commercially available insulin glulisine by replacing phenylalanine (Phe) at position B1 with glycine (Gly), and replacing threonine (Thr) with leucine (Leu) at position B27 of the B chain.

US2015/0118710A1 describes a similar process in which the yeast-derived Kexin enzyme creates insulin glargine. However, the limitation of this prior art is that the B-chain must end with two Arginine amino acid residues. Recognizing this limitation, the claims of US2015/0118710A1 were limited to the long-acting insulin glargine.

SUMMARY

There is provided a formula-specific method for synthesizing functional insulin derivatives. The method improves upon the current manufacturing process by genetically modifying a yeast, such as *Pichia pastoris*, or a bacteria, such as *Escherichia coli*, to concurrently express sortase from the bacteria *Staphylococcus aureus*, and a single chain peptide containing the sequence Leucine-Proline-X-Threonine, where X is any amino acid residue.

DETAILED DESCRIPTION

Figure 1:
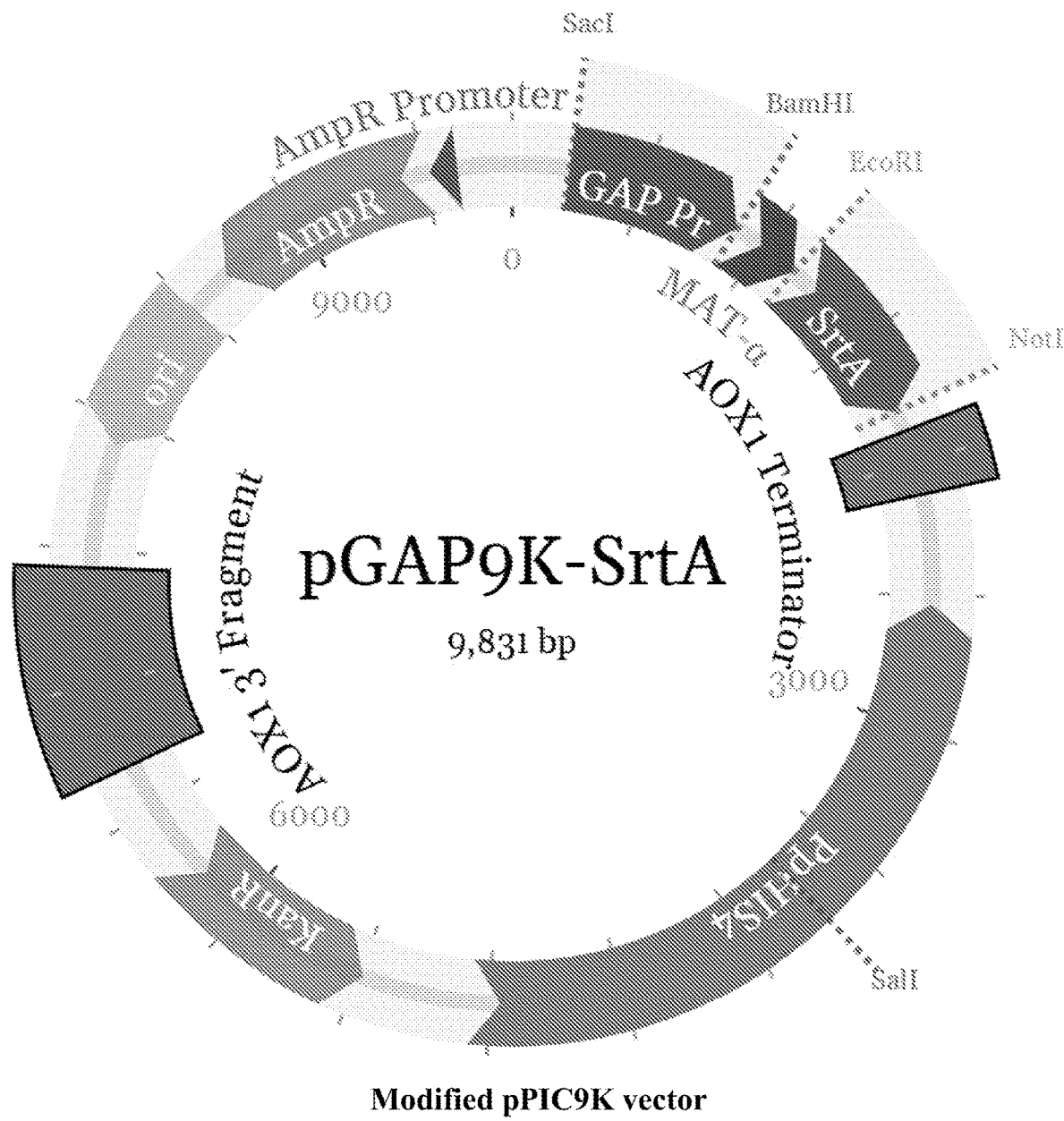
FIG. 1 shows the modifications to the initial pPIC9K vector for constitutive expression of sortase. The vector is linearized at the SalI site prior to electroporation.
Figure 2:
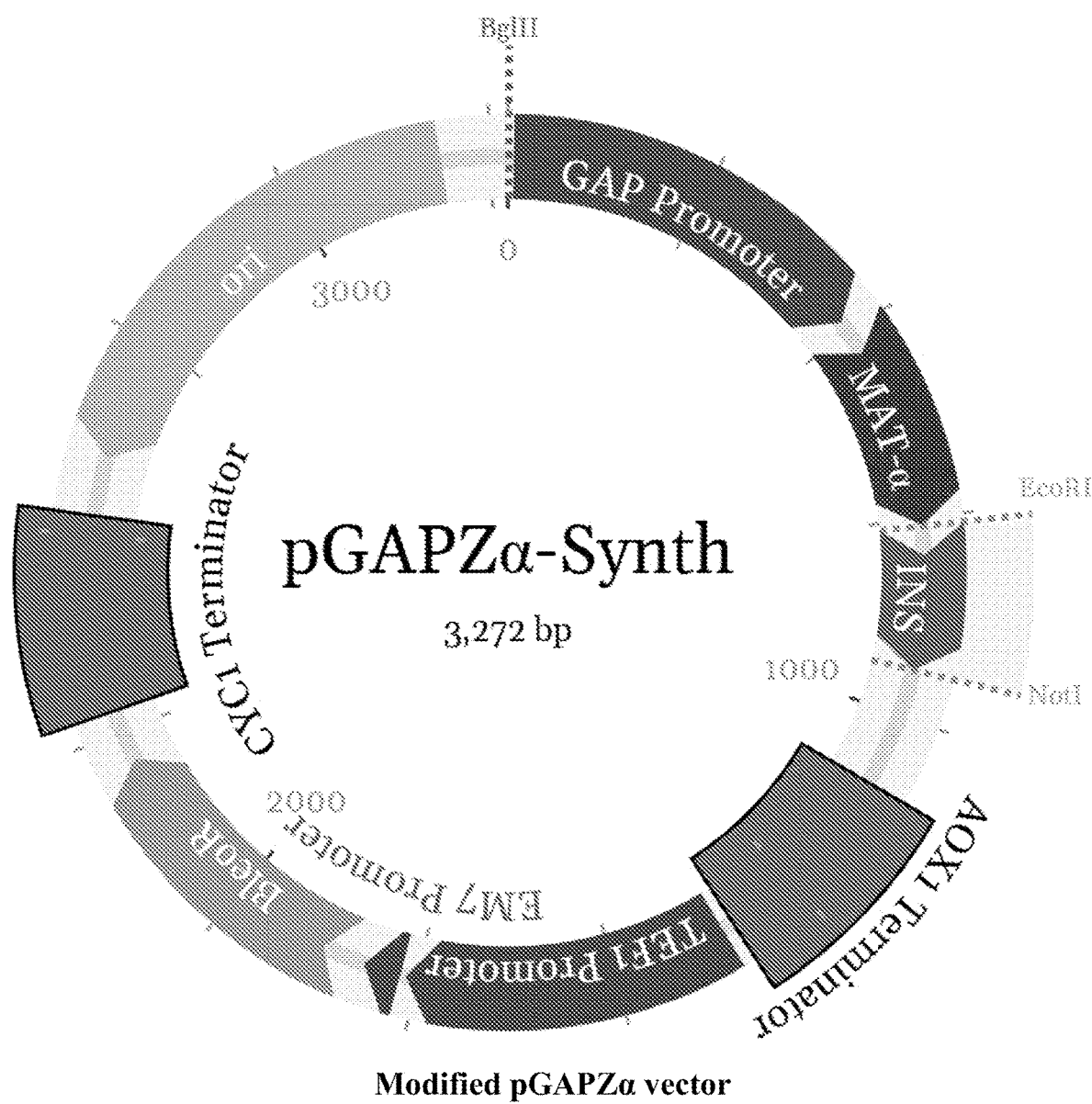
FIG. 2 shows the modifications to the initial pGAPZα vector for constitutive expression of the single chain peptide insulin derivative precursor. The vector is linearized at the BglII site prior to electroporation.
Figure 3:
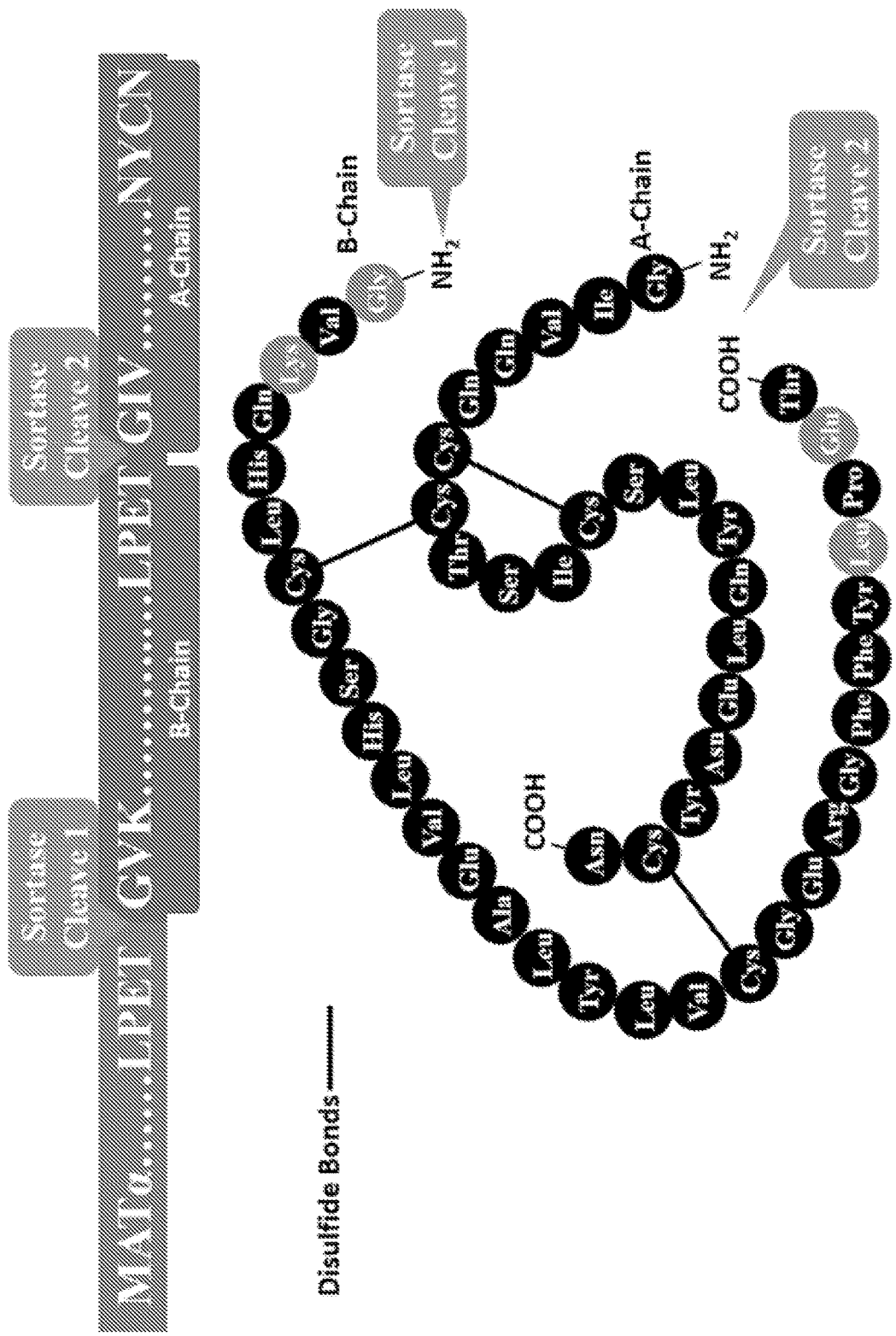
FIG. 3 shows the sites of cleavage for the insulin derivative precursor and the resulting folded structure.
Figure 4:
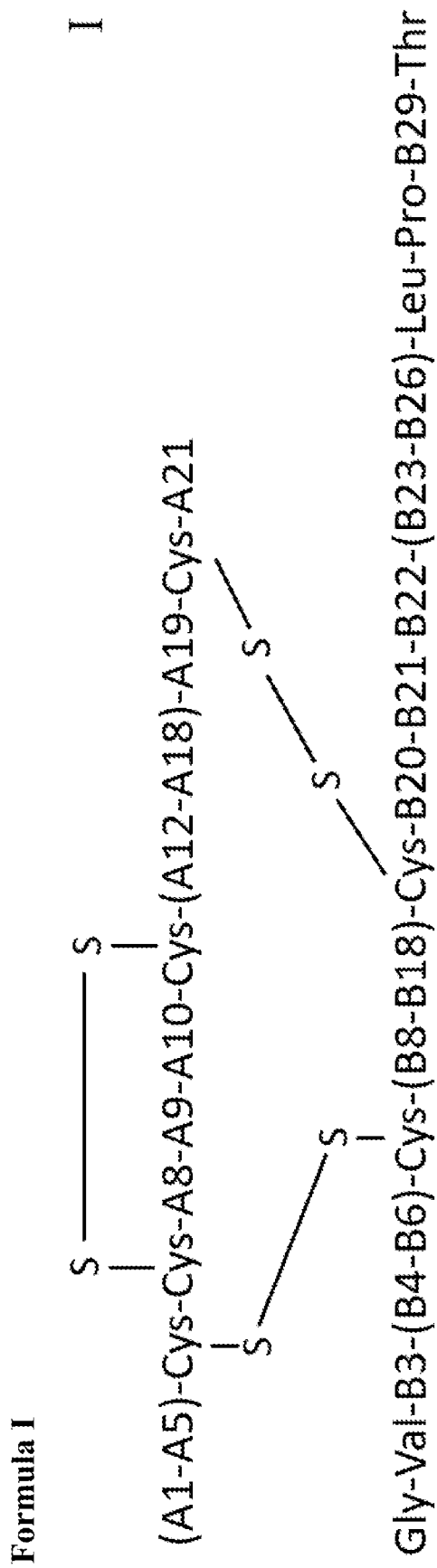
FIG. 4 shows Formula I as used in the claims section to establish relative positions and bonds of amino acid residues in various insulin derivatives created by the disclosed process.

The object of the present invention is to prepare cost-effective insulin derivatives which after administration, in particular after subcutaneous administration, have similar properties as commercially available insulin derivatives.

It is further an object of the present invention to provide a process for the preparation of the insulin derivatives having the terminal B-chain motif: Leucine-Proline-X-Threonine, where X represents any amino acid residue, and in which both the A-chain and B-chain begin with Glycine.

Insulin derivatives are derivatives of naturally occurring insulins, namely human insulin (see SEQ ID No. 3=A-chain of human insulin; see SEQ ID No. 4=B-chain of human insulin, sequence listing) or animal insulins which differ from the corresponding, otherwise identical naturally occurring insulin by substitution of at least one naturally occurring amino acid residue and/or addition of at least one amino acid residue and/or organic residue.

Of the twenty naturally occurring amino acids which are universally encodable, the amino acids glycine (Gly), alanine (Ala), Valine (Val), leucine (Leu), isoleucine (Ile), Serine (Ser), threonine (Thr), cysteine (Cys), methionine (Met), asparagine (ASn), glutamine (Gln), phenylalanine (Phe), tyrosine (Tyr), tryptophan (Trp) and proline (Pro) are designated here as neutral amino acids, the amino acids arginine (Arg), lysine (LyS) and histidine (His) are designated as basic amino acids and the amino acids aspartic acid (Asp) and glutamic acid (Glu) are designated as acidic amino acids.

Example 3 highlights the necessity of claim 1. This process trivializes the effort required to create new insulin derivatives as no intermediate catalysts or processes would need to be developed. As the limitations laid out in example 3 only differ from human insulin by two amino acid residues at positions B1 and B27, this method would allow for rapid prototyping of insulin derivatives in parallel cell lines. Once the right formulation is experimentally determined, a different method of manufacturing could be devised.

Because *Pichia pastoris* has recently received recognition for efficient recombinant expression of proteins, the first example will point to a practical approach of making the two modifications on the same host organism. However, it is possible that multiple host organisms could achieve the same result, if incubated separately.

Example 1

Following the procedure laid out by Zhao et al. published in March of 2017, the expression of sortase is achieved extracellularly by modifying the commercially available pPIC9K vector to use the GAP Promoter by using the restriction enzyme sites SacI and BamHI. Then, using the genetic material of *Staphylococcus aureus* from cell line ATCC 35556, the gene encoding sortase (SrtA) is inserted to the modified pPIC9K vector with the restriction enzymes EcoRI and NotI. The modified vector is linearized by the SalI restriction enzyme to increase transformant expression of sortase in the yeast, *Pichia pastoris*. The resulting plasmid is shown in FIG. 1. This modification is selected by growing the yeast on petri dishes with Zeocin agar.

Next, the commercially available pGAPZα vector can be used on the selected transformant *Pichia pastoris* cell line. SEQ ID No. 1 is prepared synthetically and sent in a plasmid. Once the sequence is isolated from the plasmid with the restriction enzymes EcoRI and NotI, it can be inserted in pGAPZα as shown in FIG. 2. This time, the resulting plasmid is linearized by BglII to increase expression efficiency and transformant cells are selected with Geneticin.

When the final *Pichia pastoris* transformant cell line sufficiently expresses alpha secretion factor with the single chain peptide from SEQ ID No. 2, sortase cleaves the single chain peptide as shown in FIG. 3. In FIG. 3, the differences between the resulting insulin derivative and human insulin are highlighted as gray amino acid residues.

Example 2

Another embodiment of the disclosed invention would be to express sortase using *Escherichia coli* following a procedure similar to the 2017 Wu et al. article provided as a supplementary reference. Then, the vector from FIG. 2 could be used to express the precursor peptide in *Pichia pastoris*. The resulting products would need to be extracted and combined as an intermediate step prior to final filtration. Although this is, in some ways, less efficient than example 1, it could be significantly more cost effective than the current process for similar insulin derivatives.

Example 3

The limitation imposed on the formulation of insulin derivatives by the process of preceding examples is that each chain of insulin must begin with Glycine, and the B-chain must end with Leucine-Proline-X-Threonine, where X is any amino acid. While this limitation is unique and specific, there are thousands of potentially viable insulin derivatives. When efficient expression of sortase is achieved, as in the first paragraph of example 1, the single chain peptide of SEQ ID No. 2 could arbitrarily be manipulated at relatively low cost by inserting a marginally different sequence into the commercial pGAPZα vector prior to linearization.

The invention claimed is:

1. A human insulin derivative or a physiologically tolerable salt thereof, in which the A-chain is SEQ ID No. 3, and the B-chain is a modified version of SEQ ID No. 4, in which position 1 is substituted with glycine, position 3 is substituted with lysine, position 27 is substituted with leucine, and position 29 is substituted with glutamic acid.

* * * * *